(12) United States Patent
Embrechts et al.

(10) Patent No.: US 10,201,519 B2
(45) Date of Patent: Feb. 12, 2019

(54) STABILIZED PEDIATRIC SUSPENSION OF CARISBAMATE

(71) Applicant: SK BIOPHARMACEUTICALS CO., LTD., Gyeonggi-do (KR)

(72) Inventors: Roger Embrechts, Beerse (BE); Cedric De Leersnijder, Beerse (BE)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 77 days.

(21) Appl. No.: 15/400,676

(22) Filed: Jan. 6, 2017

(65) Prior Publication Data

US 2017/0112798 A1    Apr. 27, 2017

Related U.S. Application Data

(60) Division of application No. 14/858,583, filed on Sep. 18, 2015, which is a continuation of application No. 13/570,853, filed on Aug. 9, 2012, now Pat. No. 9,161,913, which is a division of application No. 12/258,490, filed on Oct. 27, 2008, now Pat. No. 8,263,652.

(60) Provisional application No. 60/984,144, filed on Oct. 31, 2007.

(51) Int. Cl.
| | |
|---|---|
| *A61K 31/27* | (2006.01) |
| *A61K 9/00* | (2006.01) |
| *A61K 31/325* | (2006.01) |
| *A61K 47/36* | (2006.01) |
| *A61K 47/12* | (2006.01) |
| *A61K 47/26* | (2006.01) |
| *A61K 47/38* | (2006.01) |

(52) U.S. Cl.
CPC .......... *A61K 31/325* (2013.01); *A61K 9/0095* (2013.01); *A61K 31/27* (2013.01); *A61K 47/12* (2013.01); *A61K 47/26* (2013.01); *A61K 47/36* (2013.01); *A61K 47/38* (2013.01)

(58) Field of Classification Search
CPC ............................. A61K 31/27; A61K 9/0095
USPC ......................................................... 514/489
See application file for complete search history.

(56) References Cited

U.S. PATENT DOCUMENTS

| 3,265,728 A | 8/1966 | Bossinger et al. ............ 260/482 |
| 5,700,814 A | 12/1997 | François et al. .............. 514/321 |
| 6,103,759 A | 8/2000 | Choi et al. .................... 514/489 |
| 7,078,436 B2 | 7/2006 | Plata-Salaman et al. ..... 514/483 |
| 7,378,436 B2 | 5/2008 | Fish et al. ..................... 514/408 |
| 8,263,652 B2 | 9/2012 | Embrechts et al. .......... 514/489 |
| 9,161,913 B2 | 10/2015 | Embrechts et al. .......... 514/489 |
| 2008/0045583 A1 | 2/2008 | Delmarre et al. ............. 514/424 |
| 2008/0090903 A1 | 4/2008 | Pandey et al. ................ 514/489 |

OTHER PUBLICATIONS

Office Action (Restriction Requirement) dated Dec. 1, 2010 in U.S. Appl. No. 12/258,490.
Office Action (Non-final) dated Dec. 21, 2011 in U.S. Appl. No. 12/258,490.
Office Action (Non-final) dated Dec. 7, 2012 in U.S. Appl. No. 13/570,853.
Office Action (Non-final) dated Oct. 6, 2014 in U.S. Appl. No. 13/570,853.
Office Action (Non-final) dated Mar. 25, 2016 in U.S. Appl. No. 14/858,583.
Office Action (Final) dated Oct. 7, 2016 in U.S. Appl. No. 14/858,583.

*Primary Examiner* — Jennifer M Kim
(74) *Attorney, Agent, or Firm* — Harness, Dickey & Pierce, P.L.C.

(57) ABSTRACT

The present invention provides a stabilized pharmaceutical suspension of carisbamate for pediatric and adult use. More particularly, the suspension is stabilized with hypromellose (HFMC) to prevent crystal growth of the suspended particles and to prevent re-crystallization of the drug product with change in polymorphic form.

14 Claims, No Drawings

STABILIZED PEDIATRIC SUSPENSION OF CARISBAMATE

CROSS-REFERENCE TO RELATED APPLICATIONS

This application is a divisional application of U.S. Continuation application Ser. No. 14/858,583, filed 18 Sep. 2015, which claims priority to U.S. Divisional application Ser. No. 13/570,853, filed 9 Aug. 2012, which claims priority to U.S. application Ser. No. 12/258,490, filed 27 Oct. 2008 which claims the benefit of and priority to U.S. Provisional Application No. 60/984,144, filed 31 Oct. 2007. The entire disclosures of the applications identified in this paragraph are incorporated herein by reference.

FIELD OF THE INVENTION

The present invention provides a stabilized pharmaceutical suspension of carisbamate for pediatric and adult use. More particularly, the suspension is stabilized to prevent crystal growth of the suspended particles and to prevent re-crystallization of the drug product with change in polymorphic form. In addition, the formulation is taste masked to provide a formulation that can be easily administrated to patients who have difficulty swallowing tablets or capsules, e.g., pediatric patients.

BACKGROUND OF THE INVENTION

The pharmaceutical industry employs a variety of dosage formulations for orally administering medicinal agents to patients. Typical formulations for oral administration include liquid solutions, emulsions, or suspensions, as well as solid forms such as capsules or tablets. Solid oral dosage formulations are usually intended for adults who car easily swallow large tablets whole, the often disagreeable taste of the active ingredient need not be taken into account in formulating the medicine, except for the provision of means to prevent the taste from being apparent during the short time that the medicine is in the mouth. Such means may include the provision of an appropriate coating on the tablet, the use of a capsule form (the gelatin outer shell of the capsule keeps the active ingredient inside until the capsule has been swallowed), or simply firmly compressing a tablet so that it will not begin to disintegrate during the short time that it is intended to be in the mouth.

Children, older persons, and many other persons have difficulty swallowing whole tablets and even capsules. Therefore, it is often desirable to provide the medicine either in liquid form or in a chewable solid form or an alternative solid form, e.g., small particles which can be sprinkled onto soft food and swallowed intact with the food, in addition to the tablet or capsule intended to be swallowed whole. A oral liquid dosage form has many advantages for pediatric patients and for elderly patients. Many medicines have bitter or an otherwise disagreeable taste and this can be a significant problem. A further requirement of any dosage form is that it must be bioavailable; that is, once the formulation reaches the stomach, the formulation should release the active ingredient rapidly and completely to ensure that substantially the entire amount of the active ingredient is absorbed.

For some medicines the limited solubility of the drug in water can be a problem in formulation liquid oral dosage forms and in this case a suspension is often used. However, a suspension can present it's own type of problem if the drug has some solubility in water the tiny particles held in an aqueous suspension can change in crystal form or size. This can present problems in maintaining proper bioavailability either because crystal size can affect absorption rate or because the re-crystallization process can alter the polymorphic form of the suspended crystals and the altered form may have a different bioavailability. Thus there is a need for a suspension formulation that reduces the rate of re-crystallization and/or change in polymorphic form of a slightly soluble crystalline compound such as carisbamate.

SUMMARY OF THE INVENTION

The present invention is directed to a pharmaceutical formulation comprising a suspension of carisbamate particles in water with the addition of hypromellose from about 1.8 to about 2.0 mg/ml to stabilize the suspension to act as vetting agent and to control crystal growth and re-formation and to stabilize crystal structure.

In another aspect is a method of formulating such a suspension comprising: (a) preparing one solution by dissolving the sodium benzoate in approximately 30% of the total water volume at room temperature 22 C; (b) adding the citric acid, the sucralose and the raspberry flavor with mixing; (c) preparing a second solution dispersing the hypromellose (HPMC) and the carisbamate in approximately 70% of the total water volume at 22 C with mixing; (d) adding the first solution to the second while mixing to form the stabilized suspension and (e) adding the citric acid monohydrate to adjust the pH of the final formulation to between pH 3.5 and 4.5 preferably with a target pH of 4.0.

In another aspect of the invention are methods of treating a condition selected from; epilepsy, neuropathic pain, tremor, epileptogenesis, neuroprotection, schizophrenia, non-schizophrenic psychoses, behavioral disturbances associated with neurodegenerative disorders, e.g. in dementia, behavioral disturbances in mental retardation and autism, bipolar mania, depression, and anxiety, in need thereof, which comprises administering to the mammal a therapeutically effective amount of any of the pharmaceutical compositions of the present invention.

DETAILED DESCRIPTION OF THE INVENTION

A variety of substituted phenyl alkyl carbamate compounds described in U.S. Pat. No. 3,265,728 to Bossinger et al. have anticonvulsant activity in mammals, and thus their utility in treating diseases such as epilepsy in humans.

More specifically, the compound S-(2-(2-chlorophenyl)-2-hydroxyethyl) oxocarboxamide, (which may also be properly named 1,2-ethanediol, {1-2-chlorophenyl]-2-carbamate, [S]-) hereinafter referred to as "carisbamate", (shown below) is presently being developed for marketing as adjunctive therapy for the treatment of adults and children with partial onset seizures.

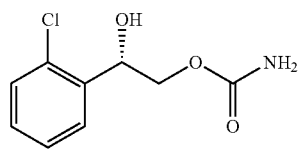

Carisbamate
1,2-ethanediol,{1-2-chlorophenyl]-2-carbamate,[S]

The present invention provides an aqueous suspension of carisbamate intended primarily for pediatric use, or for patients who cannot swallow tablets Carisbamate and related compounds can be prepared following the processes disclosed in U.S. Pat. No. 6,103,759 the disclosure of which is hereby incorporated by reference herein.

The present invention is directed to a pharmaceutical formulation comprising a stabilized suspension of carisbamate particles in water with the addition of; a wetting agent, a crystal stabilization agent, buffering agents, antimicrobial agents and flavoring to improve taste.

Carisbamate has been problematic to formulate in an aqueous suspension because it is slightly soluble in water, i.e., more than 2 mg/ml, so that temperature changes can cause the carisbamate particles to dissolve in the aqueous suspension medium and then re-crystallize out on the remaining carisbamate crystals and change the size of the resulting crystals or re crystallize in a different polymorphic form. This change in crystal size or polymorphic form, e.g., from Form A to Form B, can cause an undesirable change in bioavailability of the suspension. The present invention is based in part on the discovery that the addition of hypromellose (hydroxypropyl methyl cellulose or HPMC) in the proper concentration will prevent or stabilize this crystal growth and therefore serve to stabilize the suspension maintaining bioavailability and improving shelf life of the product.

Hypromellose (HPMC) is used in the pharmaceutical industry in a variety of ways including in the fabrication of hydrophilic matrices in controlled release drug formulations and as a wetting agent and carrier in solid dispersions of solid compounds. The present invention is based, in part, on the discovery that the addition of hypromellose (hydroxypropyl methyl cellulose or HPMC) in amounts from about 1.8 to about 22.0 mg/ml acts to stabilize the crystals in an aqueous suspension of carisbamate and to control crystal growth and re formation and therefore stabilize crystal structure and maintain polymorphic form. HPMC can also act as a wetting agent in the present formulation. The addition of HPMC to the aqueous suspension of carisbamate will dramatically slow the change in crystal size and the dissolution and recrystallization of suspended crystals of carisbamate and therefore the transition from polymorph A to polymorph B. Without the addition of the proper concentration of HPMC to stabilize the suspension the alteration in carisbamate crystal size and the change in polymorphic form can cause, over time, an undesirable change in bioavailability of the active drug.

The oral compositions optionally may include additional ingredients known in the art of formulation such as sweetening agents, flavoring substances, viscosity regulating agents and the like ingredients. For example, the physical stability of a suspension may be enhanced by the addition to the solution of a pharmaceutically acceptable suspending agent.

The bitter taste of carisbamate and the buffer, and the unpleasant taste associated with the pH of some formulas optionally may be masked by one or more intense sweetening agents such as; sucralose, saccharin, sodium or potassium or calcium saccharin, acesulfame potassium or sodium cyclamate or by use of sugars such as mannitol, fructose, sucrose, maltose and the like in the present invention. The concentration of the sweetening agent may range from 0.04% to 0.5% and in particular is about 0.4%. A preferred sweetener in the present invention is sucralose at about 4 mg/ml.

The palatability of the subject solutions optionally may be optimized further by the addition of one or more flavoring substances. Suitable flavoring substances are fruit flavors such as cherry, raspberry, black currant or strawberry flavor, or stronger flavors, such as Caramel Chocolate flavor, Mint Cool flavor, Fantasy flavor and the like. The use of a raspberry fruit flavor was found to yield very good taste masking results in the present compositions. The total concentration of the flavoring substances may range from 0.1 to 5.0 mg/ml, preferably from 0.3% to 3.0 mg/ml and most preferably from 1.5 to 2.5 mg/ml.

The pharmacokinetic properties of the aqueous suspensions according to the present invention further may depend to a limited extent on the physico-chemical properties of the carisbamate solid, such as the particle size and crystal form.

Aqueous compositions according to the present invention conveniently further comprise a suspending agent and a wetting agent, and optionally one or more of a preservative or antimicrobial agent, a buffer or pH-regulator and an isotonizing agent. Particular ingredients may function as two or more of these agents simultaneously. e.g. behave like a preservative and a buffer, or behave like a buffer and an isotonizing agent.

Suitable suspending agents for use in the aqueous suspensions according to the present invention are cellulose derivatives, e.g. methyl cellulose, sodium carboxymethyl cellulose and hydroxypropyl methyl cellulose, polyvinylpyrrolidone, alginates, chitosan, dextrans, gelatin, polyethylene glycols, polyoxyethylene- and polyoxypropylene ethers. Preferably microcrystalline cellulose and sodium carmellose are used in a concentration of 0.5 to 25 mg/ml, more preferably 3.0 to 15 mg/ml, and most preferably 13 mg/ml.

Suitable wetting agents for use in the aqueous suspensions according to the present invention are; hypromellose (HPMC), polyoxyethylene derivatives of sorbitan esters, e.g. polysorbate 20 and polysorbate 80, lecithin, polyoxyethylene- and polyoxypropylene ethers, sodium deoxycholate. Preferably hypromellose 5 mPa·s is used in a concentration of 0.1 to 20 mg/ml, more preferably 1.0 to 15 mg/ml, and most preferably 10 mg/ml. Thus the HPMC in the suspension of the present invention plays two role, as a crystal stabilizer and as a wetting agent In order to prevent the growth of micro-organisms such as bacteria, yeasts and fungi in the oral compositions which are likely to be used repeatedly, a preservative agent may be added. Preservatives are antimicrobials and anti-oxidants which can be selected from the group consisting of benzoic acid, sodium benzoate, benzyl alcohol, butylated hydroxyanisole, butylated hydroxytoluene, chlorbutol, a gallate, a hydroxybenzoate, EDTA. Suitable preservatives should be physicochemically stable and effective in the pH range mentioned above.

The concentration of the preservatives may range from 0.05% to 1%, particularly from 0.1% to 0.5%, and most particularly is about 0.2%. The most preferred preservative is benzoic acid used at about 2 mg/ml. However in the present invention the most preferred preservative for ease of formulation is sodium benzoate used in a concentration of 0.1 to 2.0 mg/ml, more preferably 1.0 to 1.5 mg/ml, and most preferably 1.18 mg/ml.

In addition, particular buffering agents can be used to maintain the pH of the aqueous suspension. Particularly preferred is the use of a mixture of citric acid monohydrate is used at a conc. of 0.1 to 2.0 mg/ml and preferably 1.0 to 1.5 mg/ml and most preferably 1.3 mg/ml.

EXAMPLE

The following example is provided to further define the invention without, however, limiting the invention to the particulars of this example.

TABLE 1

Table 2: Ingredients, concentrations (mg/ml) and function:

| Ingredient | Concentration, mg/ml | Function |
|---|---|---|
| Carisbamate | 20 | Active ingredient (API) |
| Sodium benzoate* | 1.18 | Antimicrobial preservative |
| Citric acid monohydrate | 1.3 | pH-regulator, buffering agent, Potentiating agent for sodium benzoate |
| Microcrystalline cellulose and sodium carmellose | 13 | Suspending agent |
| Hypromellose 5 mPa · s | 10 | Wetting agent, protective colloid |
| Sucralose | 4 | Sweetener |
| Raspberry | 2 | Flavor |
| Purified water | q.s ad 1 ml | Vehicle |

*1.18 mg sodium benzoate = 1 mg benzoic acid
Release pH: 3.5-4.5 (Target: pH 4.0)

In formulating the above example one solution is made by dissolving the sodium benzoate in approximately 30% of the total water volume at room temperature 22 C along with the citric acid, the sucralose and the raspberry flavor. Sodium benzoate is used instead of benzoic acid because sodium benzoate dissolves easily in water at room temperature and benzoic acid needs to be dissolved by heating the water and it is difficult to disperse the HPMC in the resulting benzoic acid solution because of the formation of un-dispersible agglomerates.

A second solution is made by dispersing the suspending agent, hypromellose (HPMC) and the API, i.e., carisbamate in approximately 70% of the total water volume at 22 C. The first solution is then added to the API-HPMC dispersion while mixing to form the stabilized suspension. The citric acid monohydrate is added to adjust the pH of the final formulation to between pH 3.5 and 4.5 preferably with a target pH of 4.0.

The term "therapeutically effective amount" as used herein means that amount of active compound or pharmaceutical agent that elicits the biological or medicinal response in a tissue, system, animator human that is being sought by a researcher, veterinarian, medical doctor or other clinician, which includes alleviation of the symptoms of the disease being treated.

The term "excipient," as used herein, refers to any inert substance that may be combined with an active agent for preparing convenient dosage forms, including, for example, diluents, binders, lubricants, disintegrants, colors, flavors and sweeteners.

In view of the usefulness of carisbamate in the treatment of a number of disorders, the present invention also concerns a pharmaceutical composition as described hereinbefore for use as a medicament in the treatment of epilepsy, neuropathic pain, tremor, epileptogenesis, neuroprotection, schizophrenia, non-schizophrenic psychoses, behavioral disturbances associated with neurodegenerative disorders, e.g. in dementia, behavioral disturbances in mental retardation and autism, bipolar mania, depression, anxiety.

In addition, the present invention concerns the use of a composition as described hereinbefore for the preparation of a medicament for treating; epilepsy, neuropathic pain, tremor, epileptogenesis, neuroprotection, schizophrenia, non-schizophrenic psychoses, behavioral disturbances associated with neurodegenerative disorders, e.g. in dementia, behavioral disturbances in mental retardation and autism, bipolar mania, depression, anxiety. The present invention further concerns a method of treating warm-blooded animals, in particular humans suffering from epilepsy, neuropathic pain, tremor, epileptogenesis, neuroprotection, schizophrenia, non-schizophrenic psychoses, behavioral disturbances associated with neurodegenerative disorders, e.g. in dementia, behavioral disturbances in mental retardation and autism, bipolar mania, depression and anxiety said method comprising the administration of a therapeutically effective amount of an aqueous suspension as described hereinbefore. Therapeutically effective amounts of carisbamate are from 50 to 1200 mg total daily dose administered in from one to four equal doses.

What is claimed is:

1. A process for forming a pharmaceutical composition in the form of a stabilized aqueous suspension comprising the steps of:
   (a) preparing a solution by dissolving a preservative agent in approximately 30% of the total water volume at room temperature;
   (b) adding a buffering agent, a sweeting agent and a flavor thereto with mixing;
   (c) preparing a dispersion by dispersing hypromellose (HPMC) and carisbamate in approximately 70% of the total water volume at room temperature with mixing;
   (d) adding the solution to the dispersion while mixing to form a stabilized suspension; and
   (e) adding a buffering agent to adjust the pH of the final formulation to between pH 3.5 and 4.5.

2. The process according to claim 1, wherein the preservative agent is selected from the group consisting of benzoic acid, sodium benzoate, benzyl alcohol, butylated hydroxyanisole, butylated hydroxytoluene, chlorbutol, gallate, hydroxybenzoate and EDTA.

3. The process according to claim 2, wherein the preservative agent is sodium benzoate.

4. The process according to claim 1, wherein the buffering agent is citric acid.

5. The process according to claim 1, wherein the sweeting agent is selected from the group consisting of sucralose, saccharin, sodium saccharin, potassium saccharin, calcium saccharin, acesulfame potassium, sodium cyclamate, mannitol, fructose, sucrose and maltose.

6. The process according to claim 5, wherein the sweeting agent is sucralose.

7. The process according to claim 1, which further comprises adding at least one selected from the group consisting of a suspending agent, a wetting agent and an isotonizing agent.

8. The process according to claim 7, wherein the suspending agent is selected from the group consisting of methyl cellulose, sodium carboxymethyl cellulose, hydroxypropyl methyl cellulose, polyvinylpyrrolidone, alginates, chitosan, dextrans, gelatin, polyethylene glycols, polyoxyethylene ethers and polyoxypropylene ethers.

9. The process according to claim 8, wherein the suspending agent includes microcrystalline cellulose and sodium carmellose.

10. The process according to claim 7, wherein the wetting agent is selected from the group consisting of polyoxyethylene derivatives of sorbitan esters, lecithin, polyoxyethylene ethers, polyoxypropylene ethers and sodium deoxycholate.

11. The process according to claim 7, wherein the isotonizing agent is selected from the group consisting of mannitol and phosphate buffer.

12. The process according to claim 1, wherein the stabilized aqueous suspension comprises:
 a) from about 10 to about 30 mg/ml of carisbamate;
 b) from about 5 to about 15 mg/ml of hypromellose; and
 c) water.

13. The process according to claim 1, wherein the pharmaceutical composition comprises about 20 mg/ml carisbamate, about 1.18 mg/ml sodium benzoate, about 1.3 mg/ml citric acid monohydrate, about 13 mg/ml microcrystalline cellulose and sodium carmellose, and about 10 mg/ml hypromellose.

14. The process according to claim 1, wherein the hypromellose stabilizes the crystal structure and/or maintains polymorphic form of carisbamate.

\* \* \* \* \*